US012578333B2

(12) United States Patent
Wang et al.

(10) Patent No.: US 12,578,333 B2
(45) Date of Patent: Mar. 17, 2026

(54) AEROSOL BIOSENSORS AND RELATED ASPECTS FOR PATHOGEN DETECTION

(71) Applicant: THE JOHNS HOPKINS UNIVERSITY, Baltimore, MD (US)

(72) Inventors: Chao Wang, Ellicott City, MD (US); Hongpeng Jia, Pikesville, MD (US); Mukund Madhav Goyal, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 554 days.

(21) Appl. No.: 17/998,756

(22) PCT Filed: May 18, 2021

(86) PCT No.: PCT/US2021/032892
§ 371 (c)(1),
(2) Date: Nov. 14, 2022

(87) PCT Pub. No.: WO2021/236589
PCT Pub. Date: Nov. 25, 2021

(65) Prior Publication Data
US 2023/0341390 A1     Oct. 26, 2023

Related U.S. Application Data

(60) Provisional application No. 63/026,594, filed on May 18, 2020.

(51) Int. Cl.
*G01N 33/569* (2006.01)
*G01N 27/327* (2006.01)
*G01N 33/543* (2006.01)

(52) U.S. Cl.
CPC ... *G01N 33/56983* (2013.01); *G01N 27/3271* (2013.01); *G01N 27/3278* (2013.01);
(Continued)

(58) Field of Classification Search
CPC ........... G01N 33/56983; G01N 33/497; G01N 27/3276; G01N 1/40; G01N 15/0656;
(Continued)

(56) References Cited

U.S. PATENT DOCUMENTS

| | | | |
|---|---|---|---|
| 7,499,167 B2 | 3/2009 | Laudo | |
| 2005/0137491 A1* | 6/2005 | Paz | A61B 5/0878 |
| | | | 600/543 |
| 2009/0056416 A1* | 3/2009 | Nair | G01N 15/0656 |
| | | | 73/28.01 |

FOREIGN PATENT DOCUMENTS

CN          111074007 A      4/2020

OTHER PUBLICATIONS

Zhang et al., "Electrical probing of COVID-19 spike protein receptor binding domain via a graphene field-effect transistor," 2020, arXiv, pp. 1-20 (Year: 2020).*
(Continued)

*Primary Examiner* — Alexander W Keeling
*Assistant Examiner* — Kaylee Tseng
(74) *Attorney, Agent, or Firm* — MH2 Technology Law Group LLP

(57)          ABSTRACT
Provided herein are methods of detecting a pathogen, such as a severe acute respiratory syndrome coronavirus-2 (SARS-CoV-2), in aerosol samples. Related devices, kits, systems, and computer program products are also provided.

18 Claims, 8 Drawing Sheets

(52) U.S. Cl.
CPC ... *G01N 33/5438* (2013.01); *G01N 2333/165* (2013.01); *G01N 2333/948* (2013.01); *G01N 2469/10* (2013.01)

(58) Field of Classification Search
CPC .............. G01N 15/01; G01N 15/0606; G01N 2469/10; G01N 2333/948; G01N 2333/165; G01N 33/5438; G01N 27/3278; G01N 27/3271; A61B 5/097; A61B 5/082
See application file for complete search history.

(56) References Cited

OTHER PUBLICATIONS

Shen et al., "Integrating Silicon Nanowire Field Effect Transistor, Microfluidics and Air Sampling Techniques For Real-Time Monitoring Biological Aerosols," 2011, Environmental Science and Technology, vol. 45, pp. 7473-7480 (Year: 2011).*
Fu et al., "Electrical probing of SARS-CoV-2 spike protein via a graphene field effect transistor," 2020, Biosensors for Pandemics—May 6, 2020—Conference Online, p. 35 (Year: 2020).*
Ladhani, "An electrostatic sampling device for point-of-care detection of bioaerosols," 2018, KTH Royal Institute of Technology, pp. 1-45 (Year: 2018).*
TSI, "Model 3062 Diffusion Dryer Instruction Manual," 2003, TSI, pp. 1-10 (Year: 2003).*
Chen et al., "Measuring Electric Charge and Molecular Coverage on Electrode Surface from Transient Induced Molecular Electronic Signal (TIMES)," 2019, Scientific Reports, vol. 9, pp. 1-10 (Year: 2019).*
Zhou et al., "Angiotensin-converting enzyme-2 overexpression improves atrial electrical remodeling through TRPM7 signaling pathway," 2017, vol. 8, pp. 78726-78733 (Year: 2017).*
Eskina, E. (Authorized officer), International Search Report and Written Opinion in corresponding International Application No. PCT/US2021/032892 mailed on Aug. 26, 2021, 9 pages.
Giwan Seo et al. Rapid Detection of COVID-19 Causative Virus (SARS-CoV-2) in Human Nasopharyngeal Swab Specimens Using Field-Effect Transistor-Based Biosensor. ACS Nano. Apr. 28, 2020;14(4):5135-5142 doi: 10.1021/acsnano.0c02823, abstract.
Pan M. et al. Collection, particle sizing and detection of airborne viruses. J Appl Microbiol. Dec. 2019;127 (6):1596-1611 doi: 10.1111/jam.14278, abstract, p. 1602.
Ladhani Laila et al. Sampling and detection of airborne influenza virus towards point-of-care applications. PLoS One. Mar. 28, 2017;12(3):e0174314 doi: 10.1371/journal.pone.0174314, abstract.
Lee, Sun Hwa (Authorized officer), International Preliminary Report on Patentability issued in corresponding International Application No. PCT/US2021/032892 mailed on Dec. 1, 2022, 7 pages.

* cited by examiner

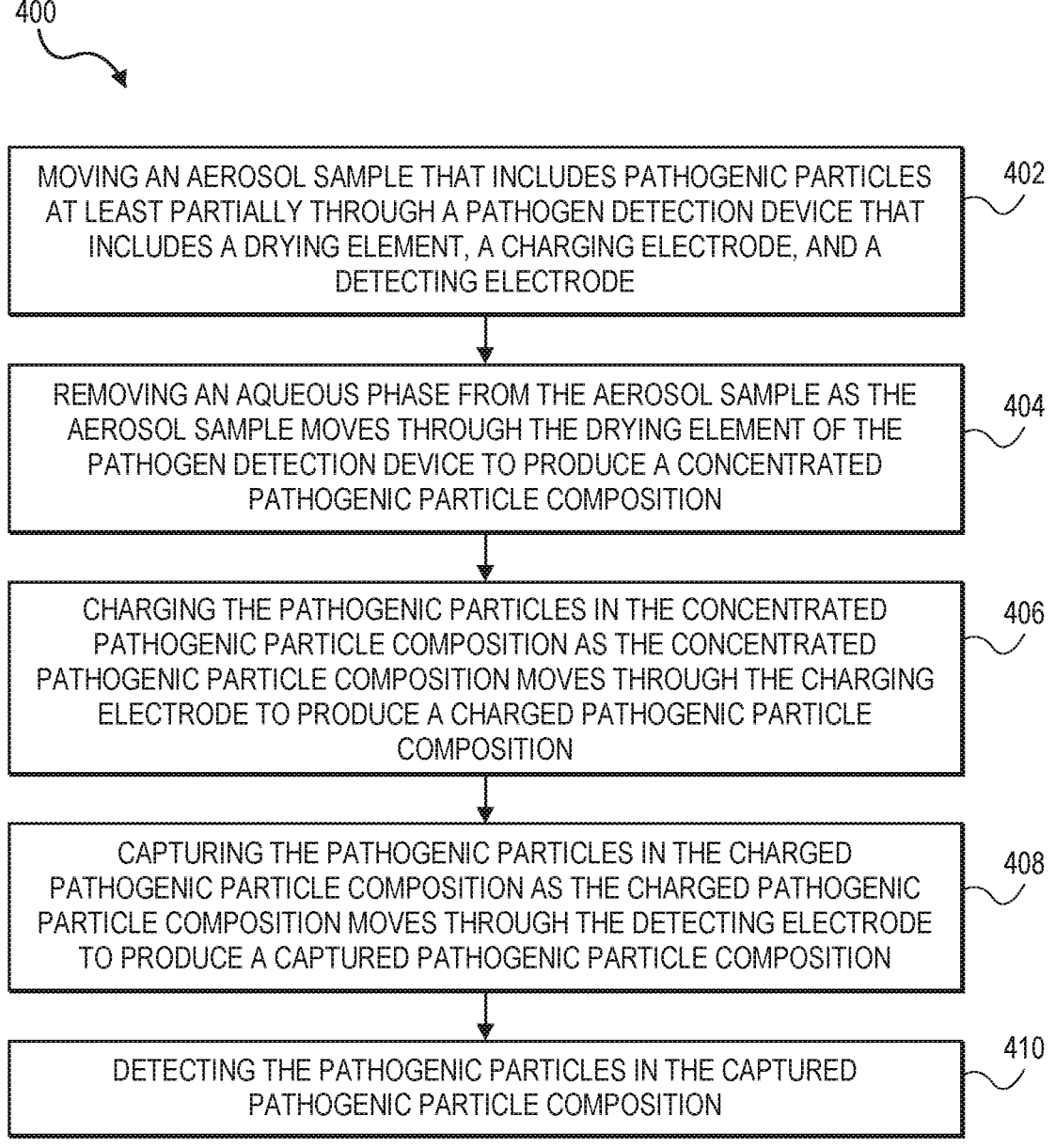

400

MOVING AN AEROSOL SAMPLE THAT INCLUDES PATHOGENIC PARTICLES AT LEAST PARTIALLY THROUGH A PATHOGEN DETECTION DEVICE THAT INCLUDES A DRYING ELEMENT, A CHARGING ELECTRODE, AND A DETECTING ELECTRODE — 402

REMOVING AN AQUEOUS PHASE FROM THE AEROSOL SAMPLE AS THE AEROSOL SAMPLE MOVES THROUGH THE DRYING ELEMENT OF THE PATHOGEN DETECTION DEVICE TO PRODUCE A CONCENTRATED PATHOGENIC PARTICLE COMPOSITION — 404

CHARGING THE PATHOGENIC PARTICLES IN THE CONCENTRATED PATHOGENIC PARTICLE COMPOSITION AS THE CONCENTRATED PATHOGENIC PARTICLE COMPOSITION MOVES THROUGH THE CHARGING ELECTRODE TO PRODUCE A CHARGED PATHOGENIC PARTICLE COMPOSITION — 406

CAPTURING THE PATHOGENIC PARTICLES IN THE CHARGED PATHOGENIC PARTICLE COMPOSITION AS THE CHARGED PATHOGENIC PARTICLE COMPOSITION MOVES THROUGH THE DETECTING ELECTRODE TO PRODUCE A CAPTURED PATHOGENIC PARTICLE COMPOSITION — 408

DETECTING THE PATHOGENIC PARTICLES IN THE CAPTURED PATHOGENIC PARTICLE COMPOSITION — 410

FIG. 4

SED 20.0kV WD15mm P.C.30  HV3  x1.000  10μm ▬▬▬    SED 20.0kV WD11mm P.C.30  HV  x5.000 5μm▬▬▬
Sample                                              Sample

AEROSOL BIOSENSORS AND RELATED ASPECTS FOR PATHOGEN DETECTION

CROSS-REFERENCE TO RELATED APPLICATIONS

This patent application is the national stage entry of International Patent Application No. PCT/US2021/032892, filed on May 18, 2021, and published as WO 2021/236589 A1 on Nov. 25, 2021, which claims the benefit of U.S. Provisional Patent Application No. 63/026,594, filed on May 18, 2020, both of which are hereby incorporated by reference herein in their entireties.

BACKGROUND

Over the last several months, the new Corona virus originally reported in Wuhan, China has caused a global pandemic [Scripps Research Institute, "COVID-19 coronavirus epidemic has a natural origin," *ScienceDaily* (2020, March 17)]. This virus was eventually named as SARS-CoV-2 (severe acute respiratory syndrome coronavirus-2) by WHO and the corresponding disease as COVID-19. As of today, SARS-CoV-2 has been known to spread among humans very easily, with the R0 estimated to be 2.2 or even above, largely due to its long viability of up to several hours in aerosols and up to days on the surface of various objects. The rising efforts on quarantine and restriction of interpersonal contacts in order to mitigate the epidemic has caused severe social panic and substantial economic consequences [NIH/National Institute of Allergy and Infectious Diseases, "New coronavirus stable for hours on surfaces: SARS-CoV-2 stability similar to original SARS virus, *ScienceDaily* (2020, March 17)].

One key to contain the propagation of COVID-19 is the early detection of SARS-CoV-2, especially in the preclinical stage when the patient has not shown symptoms such as coughing and fever. Current diagnosis of COVID-19 in the United States relies on collection of upper respiratory specimens of suspected cases and nucleic acid analysis by using reverse transcription polymerase chain reaction (RT-PCR) [Centers for Disease Control and Prevention, "*Coronavirus Disease* 2019 (*COVID-*19)" (2020)]. While this method has been widely employed, it has several disadvantages: i) Albeit recent developments, PCR-based biochemical techniques remain expensive today and it still relies on professional laboratories to run. This made the diagnosis of COVID-19 a rather prestigious resource, particularly at early stage of the epidemic when the test kits were not readily available, and extensive and nonselective diagnosis for a large crowd becomes inviable. ii) Typical nucleic acid analysis takes hours to days (with time for sample transfer included). The slow response has limited the prompt response to transmission events and has also caused challenges in tracking the source of infection. iii) It relies on pre-acquired comprehensive knowledge of the genetic sequence which was not available at early stage of the epidemic and might lose the accuracy for mutated strains. iv) In addition to these limitations, the current criteria of diagnosis sampling require tracking of contact history or clinical symptoms, leaving large chances of missed cases and unrealized contagion.

Accordingly, there is a need for additional methods, and related aspects, for a robust, cost-effective biosensing strategy in order to cope with the unprecedented challenge and pathogen detection generally.

SUMMARY

The present disclosure relates, in certain aspects, to methods, devices, kits, systems, and computer readable media of use in detecting pathogens, including severe acute respiratory syndrome coronavirus-2 (SARS-CoV-2), in aerosol samples. In certain applications, for example, the methods and related aspects involve the use of tri-layer electro-aerodynamic biosensor devices that rapidly detect pathogens in patient, environmental, and other aerosolized samples types. These and other aspects will be apparent upon a complete review of the present disclosure, including the accompanying figures.

In one aspect, the present disclosure provides a method of detecting a pathogen in an aerosol sample. The method includes (a) moving at least one aerosol sample that comprises one or more pathogenic particles (e.g., one or more virus, one or more bacteria, and/or the like) at least partially through a pathogen detection device (e.g., comprising a tri-layer electro-aerodynamic device or the like) that comprises at least one drying element, at least one charging electrode, and at least one detecting electrode, and (b) removing at least a portion of an aqueous phase from the aerosol sample as the aerosol sample moves at least proximal to the drying element of the pathogen detection device to produce at least a concentrated pathogenic particle composition. The method also includes charging at least some of the pathogenic particles in the concentrated pathogenic particle composition as the concentrated pathogenic particle composition moves at least proximal to the charging electrode to produce a charged pathogenic particle composition, (d) capturing at least some of the pathogenic particles in the charged pathogenic particle composition as the charged pathogenic particle composition moves at least proximal to the detecting electrode to produce a captured pathogenic particle composition, and (e) detecting at least some of the pathogenic particles in the captured pathogenic particle composition, thereby detecting the pathogen in the aerosol sample.

In another aspect, the present disclosure provides a method of detecting a severe acute respiratory syndrome coronavirus-2 (SARS-CoV-2) in an aerosol sample. The method includes (a) moving at least one aerosol sample that comprises one or more SARS-CoV-2 particles at least partially through a SARS-CoV-2 detection device that comprises at least one drying element, at least one charging electrode, and at least one detecting electrode, which detecting electrode comprises one or more operably connected angiotensin-converting enzyme 2 (ACE2) receptors, and (b) removing at least a portion of an aqueous phase from the aerosol sample as the aerosol sample moves at least proximal to the drying element of the SARS-CoV-2 detection device to produce at least a concentrated SARS-CoV-2 particle composition. The method also includes (c) charging at least some of the SARS-CoV-2 particles in the concentrated SARS-CoV-2 particle composition as the concentrated SARS-CoV-2 particle composition moves at least proximal to the charging electrode to produce a charged SARS-CoV-2 particle composition, (d) capturing at least some of the SARS-CoV-2 particles in the charged SARS-CoV-2 particle composition with the ACE2 receptors as the charged SARS-CoV-2 particle composition moves at least proximal to the detecting electrode to produce a captured SARS-CoV-2 particle composition, and (e) detecting at least some of the SARS-CoV-2 particles in the captured SARS-CoV-2 particle composition, thereby detecting the SARS-CoV-2 in the aerosol sample.

In certain embodiments, the methods disclosed herein include obtaining the aerosol sample from a subject. In some embodiments, the methods disclosed herein include moving (e.g., flowing or the like) the aerosol sample at least partially through the detection device by a subject exhaling, spitting, sneezing, and/or coughing the aerosol sample into the detection device.

In some embodiments of the methods disclosed herein, the drying element comprises at least one diffusion drying element. In certain embodiments of the methods disclosed herein, the drying element comprises one or more drying agents selected from the group consisting of: silica, activated charcoal, calcium sulfate, calcium chloride, zeolite, alcohol, and acetone. In some embodiments of the methods disclosed herein, the drying element comprises one or more silica gel beads. In some embodiments of the methods disclosed herein, step (b) comprises substantially dehydrating the aerosol sample. In certain embodiments of the methods disclosed herein, the liquid phase comprises water. In certain embodiments of the methods disclosed herein, the aerosol sample comprises liquid droplets that have diameters in a range of about 0.1 μm to about 25 μm (e.g., about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, or about 24 μm in diameter), which liquid droplets comprise the pathogenic particles or the SARS-CoV-2 particles.

In certain embodiments of the methods disclosed herein, the charging electrode and/or the detecting electrode is porous. In some embodiments of the methods disclosed herein, the charging electrode and/or the detecting electrode comprises one or more nanotubes and/or nanowires. In certain of these embodiments, the charging electrode and/or the detecting electrode comprises at least about 1000 nanotubes and/or at least about 1000 nanowires. In some of these embodiments, the nanotubes and/or nanowires occupy a volume of at least about 2.0 mm³. In certain of these embodiments, the nanotubes and/or nanowires comprise cupric oxide nanowires (CuO NWs), carbon nanotubes (CNTs) and/or carbon nanowires (CNWs). In some of these embodiments, at least some of the nanotubes and/or nanowires are coated. In certain of these embodiments, at least some of the nanotubes and/or nanowires are collagen coated. In certain embodiments of the methods disclosed herein, step (e) comprises detecting the pathogenic particles and/or the SARS-CoV-2 particles via charge accumulation and/or via photoelectrochemical (PEC) sensing.

In some embodiments, wherein the charging electrode comprises a negative charge. In certain embodiments, the detecting electrode comprises a positive charge. In some embodiments, the methods disclosed herein include applying a voltage difference between the charging electrode and the detecting electrode in a range of about 0.1 volts (Vs) to about 25 Vs (e.g., about 1 V to about 10 Vs).

In certain embodiments, the detecting electrode comprises one or more operably connected binding agents that substantially specifically bind the pathogenic particles, thereby capturing at least some of the pathogenic particles in the charged pathogenic particle composition as the charged pathogenic particle composition moves at least proximal to the detecting electrode to produce the captured pathogenic particle composition. In some embodiments, the binding agents comprise at least one cognate receptor of the pathogenic particles. In certain embodiments, the detecting electrode comprises one or more nanotubes and/or nanowires and the binding agents or the ACE2 receptors are operably connected to the nanotubes and/or nanowires. In some of these embodiments, the binding agents or the ACE2 receptors are expressed on the surface of one or more cells that are operably connected to the detecting electrode. In certain embodiments, the detecting electrode comprises one or more nanotubes and/or nanowires and in the cells are operably connected to the nanotubes and/or nanowires.

In certain embodiments, the methods disclosed herein include quantifying a number of the pathogenic particles or the SARS-CoV-2 particles in the aerosol sample. In some embodiments, the methods disclosed herein include quantifying a number of the pathogenic particles or the SARS-CoV-2 particles in the aerosol sample using the formula:

$$N=kQ/n,$$

where Q is an accumulated charge calculated by integrating a detected current signal over a course of one measurement, n is an average charge number of the pathogenic particles or the SARS-CoV-2 particles, and k is a coefficient determined by charging/detection efficiencies of the charging and detecting electrodes. Typically, the pathogenic particles in the captured pathogenic particle composition or the SARS-CoV-2 particles in the captured SARS-CoV-2 particle composition induce an electrical signal that is detected in step (e). In certain embodiments, the methods disclosed herein include subtracting at least one background signal from the electrical signal that is detected in step (e).

In some embodiments, the methods disclosed herein include administering at least one therapy to a subject when the pathogen or the SARS-CoV-2 is detected in the aerosol sample obtained from the subject. In certain embodiments, the methods disclosed herein include repeating steps (a)-(e) for different aerosol samples, wherein the pathogen detection device or the SARS-CoV-2 detection device is sanitized before repeating (a)-(e) for a given different aerosol sample to at least minimize carryover contamination from a previous aerosol sample. In certain embodiments, the methods disclosed herein include completing steps (a)-(e) in less than about five minutes.

In some embodiments disclosed herein, the pathogen detection device or the SARS-CoV-2 detection device comprises a reusable portion and a disposable portion, wherein the disposable portion comprises the drying element, the charging electrode, and the detecting electrode. In certain of these embodiments, the reusable portion comprises at least one result indicator (e.g., comprising a light, a display screen, and/or the like) operably connected, or connectable, at least to the detecting electrode and wherein step (e) comprises indicating when the pathogen or the SARS-CoV-2 is detected using the result indicator. In some of these embodiments, the disposable portion comprises at least one opening that communicates at least with the drying element and wherein step (a) comprises introducing the aerosol sample into the pathogen detection device or the SARS-CoV-2 detection device through the opening. In some embodiments, a mouthpiece comprises the disposable portion.

In certain aspects, the present disclosure provides a pathogen detection device that includes a body structure that comprises at least one cavity and at least one opening that communicates with the cavity, which cavity receives at least one aerosol sample that comprises one or more pathogenic particles when the aerosol sample moves through the opening. The pathogen detection device also includes at least one drying element that communicates with the cavity. The drying element removes at least a portion of an aqueous phase from the aerosol sample to produce at least a concentrated pathogenic particle composition when the aerosol sample moves at least proximal to the drying element. The pathogen detection device also includes at least one charging electrode that communicates with the cavity. The charging electrode charges at least some of the pathogenic particles in the concentrated pathogenic particle composition to produce a charged pathogenic particle composition when the concentrated pathogenic particle composition moves at least proximal to the charging electrode. The pathogen detection device also includes at least one detecting electrode that communicates with the cavity. The detecting electrode captures at least some of the pathogenic particles in the charged pathogenic particle composition to produce a captured pathogenic particle composition when the charged pathogenic particle composition moves at least proximal to the detecting electrode. In addition, the pathogen detection device also includes at least one controller operably connected, or connectable to, at least to the detecting electrode, which controller detects at least some of the pathogenic particles in the captured pathogenic particle composition when the captured pathogenic particle composition is produced, and at least one power source operably connected, or connectable to, at least to the charging electrode, the detecting electrode, and/or the controller.

In some aspects, the present disclosure provides a severe acute respiratory syndrome coronavirus-2 (SARS-CoV-2) detection device that includes a body structure that comprises at least one cavity and at least one opening that communicates with the cavity. The cavity receives at least one aerosol sample that comprises one or more SARS-CoV-2 particles when the aerosol sample moves through the opening. The SARS-CoV-2 detection device also includes at least one drying element that communicates with the cavity. The drying element removes at least a portion of an aqueous phase from the aerosol sample to produce at least a concentrated SARS-CoV-2 particle composition when the aerosol sample moves at least proximal to the drying element. The SARS-CoV-2 detection device also includes at least one charging electrode that communicates with the cavity. The charging electrode charges at least some of the SARS-CoV-2 particles in the concentrated SARS-CoV-2 particle composition to produce a charged SARS-CoV-2 particle composition when the concentrated SARS-CoV-2 particle composition moves at least proximal to the charging electrode. The SARS-CoV-2 detection device also includes at least one detecting electrode that communicates with the cavity. The detecting electrode comprises one or more operably connected angiotensin-converting enzyme 2 (ACE2) receptors that capture at least some of the SARS-CoV-2 particles in the charged SARS-CoV-2 particle composition to produce a captured SARS-CoV-2 particle composition when the charged SARS-CoV-2 particle composition moves at least proximal to the detecting electrode. In addition, the SARS-CoV-2 detection device also includes at least one controller operably connected, or connectable to, at least to the detecting electrode, which controller detects at least some of the SARS-CoV-2 particles in the captured SARS-CoV-2 particle composition when the captured SARS-CoV-2 particle composition is produced, and at least one power source operably connected, or connectable to, at least to the charging electrode, the detecting electrode, and/or the controller.

In some aspects, the present disclosure provides a system that includes at least one pathogen detection device that comprises at least one drying element, at least one charging electrode, and at least one detecting electrode, and at least one controller operably connected, or connectable to, at least to the pathogen detection device. The controller comprises, or is capable of accessing, computer readable media comprising non-transitory computer-executable instructions which, when executed by at least one electronic processor perform at least: charging at least some pathogenic particles in a concentrated pathogenic particle composition as the concentrated pathogenic particle composition moves at least proximal to the charging electrode to produce a charged pathogenic particle composition, wherein the concentrated pathogenic particle composition is produced by removing at least a portion of an aqueous phase from an aerosol sample that comprises the pathogenic particles as the aerosol sample moves at least proximal to the drying element of the pathogen detection device; capturing at least some of the pathogenic particles in the charged pathogenic particle composition as the charged pathogenic particle composition moves at least proximal to the detecting electrode to produce a captured pathogenic particle composition; and/or detecting at least some of the pathogenic particles in the captured pathogenic particle composition.

In certain aspects, the present disclosure provides a system that includes at least one severe acute respiratory syndrome coronavirus-2 (SARS-CoV-2) detection device that comprises at least one drying element, at least one charging electrode, and at least one detecting electrode, which detecting electrode comprises one or more operably connected angiotensin-converting enzyme 2 (ACE2) receptors. The system also includes at least one controller operably connected, or connectable to, at least to the SARS-CoV-2 detection device. The controller comprises, or is capable of accessing, computer readable media comprising non-transitory computer-executable instructions which, when executed by at least one electronic processor perform at least: charging at least some SARS-CoV-2 particles in a concentrated SARS-CoV-2 particle composition as the concentrated SARS-CoV-2 particle composition moves at least proximal to the charging electrode to produce a charged SARS-CoV-2 particle composition, wherein the concentrated SARS-CoV-2 particle composition is produced by removing at least a portion of an aqueous phase from an aerosol sample that comprises the SARS-CoV-2 particles as the aerosol sample moves at least proximal to the drying element of the SARS-CoV-2 detection device; capturing at least some of the SARS-CoV-2 particles in the charged SARS-CoV-2 particle composition with the ACE2 receptors as the charged SARS-CoV-2 particle composition moves at least proximal to the detecting electrode to produce a captured SARS-CoV-2 particle composition; and/or detecting at least some of the SARS-CoV-2 particles in the captured SARS-CoV-2 particle composition.

In certain embodiments, the detection devices or systems disclosed herein are packaged as part of kits. In some embodiments of the detection devices or systems disclosed herein, the opening is structured to receive the aerosol sample from a subject. In certain embodiments of the detection devices or systems disclosed herein, the opening is structured to receive the aerosol sample from a subject when the subject exhales, spits, sneezes, and/or coughs the aerosol sample through the opening such that the aerosol sample moves at least partially through the cavity.

In some embodiments of the detection devices or systems disclosed herein, the drying element comprises at least one diffusion drying element. In certain embodiments of the detection devices or systems disclosed herein, the drying element comprises one or more drying agents selected from the group consisting of: silica, activated charcoal, calcium sulfate, calcium chloride, zeolite, alcohol, and acetone. In some embodiments of the detection devices or systems disclosed herein, the drying element comprises one or more silica gel beads. In certain embodiments of the detection devices or systems disclosed herein, the drying element is structured to substantially dehydrate the aerosol sample when the aerosol sample moves at least proximal to the drying element.

In certain embodiments of the detection devices or systems disclosed herein, the charging electrode and/or the detecting electrode is porous. In some embodiments of the detection devices or systems disclosed herein, the charging electrode and/or the detecting electrode comprises one or more nanotubes and/or nanowires. In certain embodiments of the detection devices or systems disclosed herein, the charging electrode and/or the detecting electrode comprises at least about 1000 nanotubes and/or at least about 1000 nanowires. In certain embodiments of the detection devices or systems disclosed herein, the nanotubes and/or nanowires occupy a volume of at least about 2.0 $mm^3$. In some embodiments of the detection devices or systems disclosed herein, the nanotubes and/or nanowires comprise cupric oxide nanowires (CuO NWs), carbon nanotubes (CNTs) and/or carbon nanowires (CNWs). In certain embodiments of the detection devices or systems disclosed herein, at least some of the nanotubes and/or nanowires are coated. In certain embodiments of the detection devices or systems disclosed herein, at least some of the nanotubes and/or nanowires are collagen coated. In some embodiments of the detection devices or systems disclosed herein, the detection device or system is configured to detect the pathogenic particles and/or the SARS-CoV-2 particles via charge accumulation and/or via photoelectrochemical (PEC) sensing.

In some embodiments of the detection devices or systems disclosed herein, the charging electrode is structured to generate a negative charge. In certain embodiments of the detection devices or systems disclosed herein, the detecting electrode is structured to generate a positive charge. In some embodiments of the detection devices or systems disclosed herein, the controller and/or power source is configured to effect application of a voltage difference between the charging electrode and the detecting electrode in a range of about 0.1 volts (Vs) to about 25 Vs (e.g., a range of about 1 V to about 10 Vs, or the like).

In certain embodiments of the detection devices or systems disclosed herein, the detecting electrode comprises one or more operably connected binding agents that substantially specifically bind the pathogenic particles to thereby capture at least some of the pathogenic particles in the charged pathogenic particle composition as the charged pathogenic particle composition moves at least proximal to the detecting electrode to produce the captured pathogenic particle composition. In certain embodiments of the detection devices or systems disclosed herein, the binding agents comprise at least one cognate receptor of the pathogenic particles. In certain embodiments of the detection devices or systems disclosed herein, the detecting electrode comprises one or more nanotubes and/or nanowires and the binding agents or the ACE2 receptors are operably connected to the nanotubes and/or nanowires. In some embodiments of the detection devices or systems disclosed herein, the binding agents or the ACE2 receptors are expressed on the surface of one or more cells that are operably connected to the detecting electrode. In certain embodiments of the detection devices or systems disclosed herein, the detecting electrode comprises one or more nanotubes and/or nanowires and wherein the cells that are operably connected to the nanotubes and/or nanowires.

In certain embodiments of the detection devices or systems disclosed herein, the pathogen detection device comprises a tri-layer electro-aerodynamic device. In some of the detection devices or systems disclosed herein, the controller is configured to effect quantifying a number of the pathogenic particles or the SARS-CoV-2 particles in the aerosol sample. In certain embodiments of the detection devices or systems disclosed herein, the controller detects an electrical signal induced by the pathogenic particles in the captured pathogenic particle composition or by the SARS-CoV-2 particles in the captured SARS-CoV-2 particle composition. In certain embodiments of the detection devices or systems disclosed herein, the controller is configured to subtract at least one background signal from the electrical signal that is detected.

In some of the detection devices or systems disclosed herein, the body structure comprises a reusable portion and a disposable portion in which the disposable portion comprises at least portions of the opening, the cavity, the drying element, the charging electrode, and the detecting electrode. In some of the detection devices or systems disclosed herein, the reusable portion comprises at least one result indicator (e.g., an indicator light, a display screen, etc.) operably connected, or connectable, at least to the detecting electrode and/or to the controller, which result indicator indicates when the pathogen or the SARS-CoV-2 is detected. In some of the detection devices or systems disclosed herein, the reusable portion comprises at least one handle. In some embodiments, the systems disclosed herein include multiple pathogen detection devices and/or multiple SARS-CoV-2 detection devices operably connected, or connectable to, the controller (e.g., as part of a pathogen (e.g., SARS-CoV-2) surveillance or monitoring network).

In some aspects, the present disclosure provides a computer readable media comprising non-transitory computer-executable instructions which, when executed by at least one electronic processor perform at least: charging at least some pathogenic particles in a concentrated pathogenic particle composition as the concentrated pathogenic particle composition moves at least proximal to at least one charging electrode of at least one pathogen detection device to produce a charged pathogenic particle composition, wherein the concentrated pathogenic particle composition is produced by removing at least a portion of an aqueous phase from an aerosol sample that comprises the pathogenic particles as the aerosol sample moves at least proximal to at least one drying element of the pathogen detection device; capturing at least some of the pathogenic particles in the charged pathogenic particle composition as the charged pathogenic particle composition moves at least proximal to at least one detecting electrode of the pathogen detection device to produce a captured pathogenic particle composition; and/or detecting at least some of the pathogenic particles in the captured pathogenic particle composition.

In certain aspects, the present disclosure provides a computer readable media comprising non-transitory computer-executable instructions which, when executed by at least one electronic processor perform at least: charging at least some severe acute respiratory syndrome coronavirus-2 (SARS-CoV-2) particles in a concentrated SARS-CoV-2 particle composition as the concentrated SARS-CoV-2 particle composition moves at least proximal to at least one charging electrode of at least one SARS-CoV-2 detection device to produce a charged SARS-CoV-2 particle composition, wherein the concentrated SARS-CoV-2 particle composition is produced by removing at least a portion of an aqueous phase from an aerosol sample that comprises the SARS- CoV-2 particles as the aerosol sample moves at least proximal to the drying element of the SARS-CoV-2 detection device; capturing at least some of the SARS-CoV-2 particles in the charged SARS-CoV-2 particle composition with one or more angiotensin-converting enzyme 2 (ACE2) receptors that are operably connected to at least one detecting electrode of the SARS-CoV-2 detection device the as the charged SARS-CoV-2 particle composition moves at least proximal to the SARS-CoV-2 electrode to produce a captured SARS-CoV-2 particle composition; and detecting at least some of the SARS-CoV-2 particles in the captured SARS-CoV-2 particle composition.

BRIEF DESCRIPTION OF THE DRAWINGS

The accompanying drawings, which are incorporated in and constitute a part of this specification, illustrate certain embodiments, and together with the written description, serve to explain certain principles of the methods, devices, kits, systems, and related computer readable media disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

FIG. 4 is a flow chart that schematically depicts exemplary method steps according to some aspects disclosed herein.

DEFINITIONS

Figure 1:
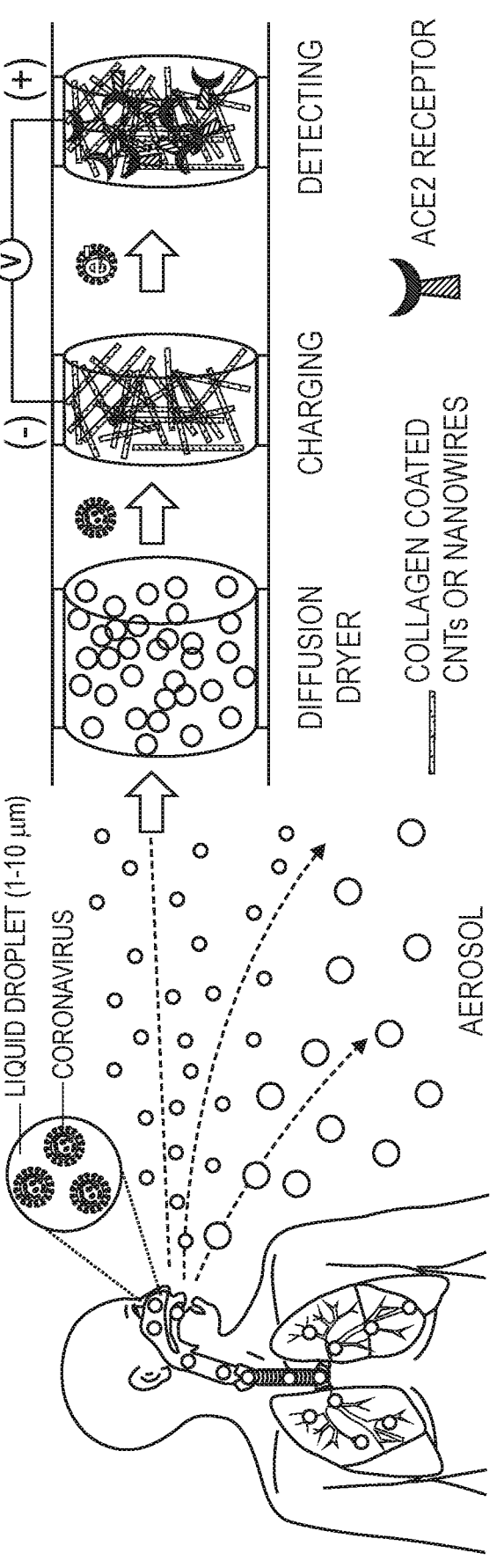
FIG. 1 schematically depicts an aerosol biosensor that uses electro-aerodynamic deposition and ACE2 receptors for SARS-CoV-2 detection according to an exemplary embodiment.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

It is also to be understood that the terminology used herein is for the purpose of describing particular embodiments only and is not intended to be limiting. Further, unless defined otherwise, all technical and scientific terms used herein have the same meaning as commonly understood by one of ordinary skill in the art to which this disclosure pertains. In describing and claiming the methods, systems, and component parts, the following terminology, and grammatical variants thereof, will be used in accordance with the definitions set forth below.

About: As used herein, "about" or "approximately" or "substantially" as applied to one or more values or elements of interest, refers to a value or element that is similar to a stated reference value or element. In certain embodiments, the term "about" or "approximately" or "substantially" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Administering: As used herein, the terms "administering" and "administration" refer to any method of providing a pharmaceutical preparation or other treatment to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

Aerosol Sample: As used herein, "aerosol sample" or "aerosolized sample" refers to a sample that comprises a suspension (e.g., a colloidal suspension) of solid particles and/or liquid droplets (e.g., suspended pathogenic particles, such as severe acute respiratory syndrome coronavirus-2 (SARS-CoV-2) particles) dispersed in air or another gas.

Angiotensin-Converting Enzyme 2: As used herein, "angiotensin-converting enzyme 2" or "ACE2" refers to a zinc containing metalloenzyme that binds or otherwise associates with coronavirus, such as SARS-CoV-2. In some embodiments, ACE2 is used as a cognate receptor of SARS-CoV-2 in the pathogen detection devices and systems disclosed herein.

Bind: As used herein, "bind," in the context of pathogen detection, refers to a state in which a first chemical structure (e.g., a pathogenic particle) is sufficiently associated a second chemical structure such that the association between the first and second chemical structures can be detected.

Binding Agent: As used herein, "binding agent" refers to a chemical structure that receives or binds other chemical structures (e.g., pathogenic particles).

Cell: As used herein, "cell" is meant to include both prokaryotic (e.g., bacterial) and eukaryotic (e.g., mammalian or plant) cells. Cells may be of somatic or germ line origin, may be totipotent or pluripotent, and may be dividing or non-dividing. Cells can also be derived from or can comprise a gamete or an embryo, a stem cell, or a fully differentiated cell. Thus, the term "cell" is meant to retain its usual biological meaning and can be present in any organism such as, for example, a bird, a plant, and a mammal, including, for example, a human, a cow, a sheep, an ape, a monkey, a pig, a dog, and a cat.

Communicate: As used herein, "communicate" refers to the direct or indirect transfer or transmission, and/or capability of directly or indirectly transferring or transmitting, something at least from one area to another area.

Detecting: As used herein, "detecting," "detect," or "detection" refers to an act of determining the existence or presence of one or more target analytes (e.g., pathogenic particles, such as severe acute respiratory syndrome coronavirus-2 (SARS-CoV-2) particles) in a sample.

Pathogen: As used herein, "pathogen" or "pathogenic particle" refers to anything that can produce a disease, condition, or disorder in a subject. In some embodiments, a pathogen includes an infectious microorganism or agent, such as a bacterium, virus, viroid, protozoan, prion, or fungus.

Receptor: As used herein, "receptor" refers to a biochemical structure that receives or binds other biochemical structures (e.g., pathogenic particles).

Sample: As used herein, "sample" means anything capable of being analyzed using a device or system disclosed herein. Exemplary sample types include environmental samples and biological samples. In some embodiments, subjects exhale, spit, sneeze, cough, and/or the like to produce aerosolized samples.

Severe Acute Respiratory Syndrome Coronavirus-2: As used herein, "severe acute respiratory syndrome coronavirus-2" or "SARS-CoV-2" refers to the coronavirus that emerged in 2019 to cause a human pandemic of an acute respiratory disease, now known as coronavirus disease 2019 (COVID-19).

Specifically Bind: As used herein, "specifically bind," in the context of pathogen detection, refers to a state in which substantially only target chemical structures (e.g., target pathogenic particles) are sufficiently associated with a corresponding or cognate binding agent, to the exclusion of non-target chemical structures, such that the association between the target chemical structures and the binding agent can be detected.

System: As used herein, "system" in the context of analytical instrumentation refers a group of objects and/or devices that form a network for performing a desired objective.

Subject: As used herein, "subject" refers to an animal, such as a mammalian species (e.g., human) or avian (e.g., bird) species. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual that is in need of therapy or suspected of needing therapy. The terms "individual" or "patient" are intended to be interchangeable with "subject." For example, a subject can be an individual who has been diagnosed with having a respiratory disease, disorder, or condition, is going to receive a therapy for a respiratory disease, disorder, or condition, and/or has received at least one therapy for a respiratory disease, disorder, or condition.

Therapy: As used herein, "therapy" or "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human.

DETAILED DESCRIPTION

The present disclosure relates, in certain aspects, to robust, highly sensitive and cost-effective aerosol biosensors for the detection of SARS-CoV-2, or other pathogens, that utilizes the ligation of this coronavirus with its cognate receptor, angiotensin-converting enzyme 2 (ACE2), or another receptor that specifically binds to a different target pathogen. For example, SARS-CoV-2 is thought to target ACE2 via the high binding affinity of its S protein to this receptor [Xu et al., "High expression of ACE2 receptor of 2019-nCoV on the epithelial cells of oral mucosa," *International Journal of Oral Science*, 12(1) (2020)]. Accordingly, in certain embodiments, the ACE2 receptor, or other binding agents, are used as a "bait" to achieve early detection of coronavirus or other pathogens without relying on advance knowledge of the given pathogen's genomic sequence.

The devices or biosensors disclosed herein detect coronavirus at concentrations <100 $TCID_{50}$ in the aerosols generated by, for example, coughing, thereby enabling, for example, real-time preclinical diagnosis of COVID-19. In some implementations, the pathogen detection strategy takes advantage of the intrinsic biological mechanism of SARS-CoV-2 targeting human lung epithelia cells and breaks through the limitations of existing nucleic acid-based assay methodologies. The devices and other aspects disclosed herein are applicable at essentially any scale, including at large-scale (e.g., for use in screening a crowd or the like). In some embodiments, the methods and other aspects disclosed herein do not rely on advance knowledge of the genetic information of the targeted pathogens and can be generally applied to various biosensor formats to provide early warning signals of epidemic in clinic and publish health systems.

As shown in FIG. 1, certain embodiments are achieved with the design of a tri-layer electro-aerodynamic device incorporated with the ACE2 receptor. In some embodiments, for every cough or other sample to be measured, the generated aerosol first passes a diffusion dryer layer (e.g., a layer of silica gel beads or another drying agent) to remove the moisture and produce airborne virus particles. In these embodiments, the airstream carrying the virus then goes through a porous electrode that induces charges onto the flowing microscale particles. The charged particles then strike another porous electrode modified with ACE2 (or cells expressing ACE2). A bias in the range of 1-10 V is typically applied between the two electrodes for charging and electrical signaling. In some embodiments, the total number of coronavirus per cough is estimated via N=kQ/n, where Q is the accumulated charge by integrating the detected current signal over the course of one measurement, n is the average charge number of the virus particles (n) estimated by assuming a linear dependence on the particle diameter (~0.1 μm) according to the Fuchs theory [Adachi et al., "Unipolar and bipolar diffusion charging of ultrafine aerosol particles," *Journal of Aerosol Science*, 16(2):109-123 (1985)], and k is a coefficient determined by the charging/detection efficiencies of the two electrodes, which can be determined, for example, by calibration of the sensor with aerosols of given concentrations of coronavirus. Owing to the high affinity of coronavirus to ACE2, the detection cross-section of SARS-CoV-2 is generally significantly larger than other virus or particles that are not specifically targeted, and thus, the detected electrical signal is predominantly induced by the targeted virus. In certain applications, improvements of the signal-to-noise ratio can be achieved by repeated measurements, and also by running control with aerosols free of coronavirus to establish the background and subtracting it from the signals in real measurements.

Figure 2:
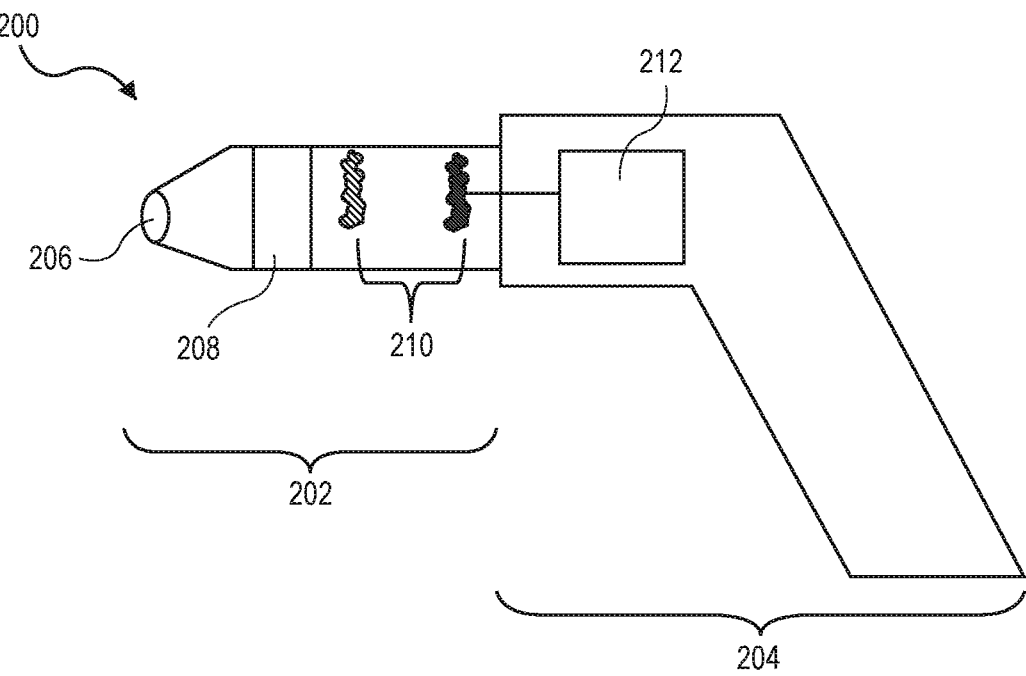
FIG. 2 schematically shows a pathogen detection device from a side view according to one exemplary embodiment.

To illustrate, FIG. 2 schematically shows a pathogen detection device from a side view according to one exemplary embodiment. As shown, pathogen detection device 200 includes a body structure that includes changeable or disposable testing portion 202 and reusable hand-held portion 204. Disposable testing portion 202 includes opening 206 that communicates with diffusion dryer chamber 208 and electrode system 210 (shown as including charging and detecting electrodes). As also shown, reusable hand-held portion 204 (shown as a handle) includes result indicator 212 (shown as a display screen) operably connected to electrode system 210. In use, a subject coughs into opening 206 such that an aerosol sample from the subject flows through and is dehydrated by diffusion dryer chamber 208 to produce a concentrated pathogenic particle composition, which is then charged as that composition flows through a charging electrode of electrode system 210 to charge pathogenic particles to produce a charged pathogenic particle composition. Detecting electrode of electrode system 210 captures charged pathogenic particles to effect detection of pathogenic particles in the aerosol sample.

Figure 3:
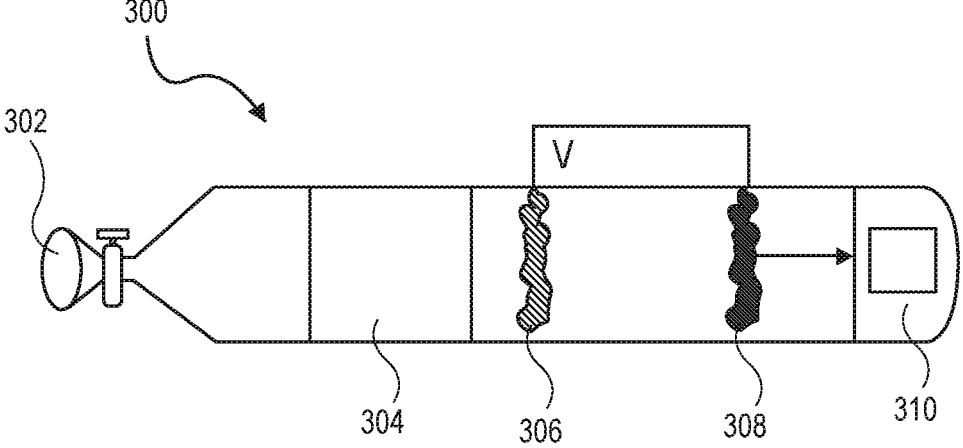
FIG. 3 schematically shows a pathogen detection device from a side view according to one exemplary embodiment.

To further illustrate, FIG. 3 schematically shows a pathogen detection device from a side view according to one exemplary embodiment. As shown, pathogen detection device 300 includes a body structure that forms a cavity that comprises diffusion dryer layer 304, charging electrode 306, and detecting electrode 308, which is operably connected to result indicator 310 for indicating testing results. Aerosol samples are introduce into the cavity of pathogen detection device 300 via opening 302, which communicates with the cavity.

The pathogen detection devices of the present disclosure include a body structure that comprises a cavity and an opening that communicates with the cavity. The cavity receives aerosol samples that comprise pathogenic particles (e.g., SARS-CoV-2 particles, etc.) when the aerosol sample moves through the opening. See, e.g., FIGS. 2 and 3. Suitable body structures are optionally fabricated using essentially any manufacturing technique, including injection molding, 3D printing, and the like. In some embodiments, the opening is structured to receive the aerosol sample from a subject (e.g., is included as part of a mouthpiece component or the like). In certain embodiments, for example, the opening is structured to receive the aerosol sample from a subject when the subject exhales, spits, sneezes, and/or coughs the aerosol sample through the opening such that the aerosol sample moves at least partially through the cavity.

The pathogen detection devices of the present disclosure also include drying element that communicates with the cavity. The drying element removes an aqueous phase from (e.g., substantially dehydrates) the aerosol sample to produce a concentrated pathogenic particle composition when the aerosol sample moves at least proximal to (e.g., through, over, under, around, and/or the like) the drying element. In some embodiments, the drying element includes a diffusion drying element. In certain embodiments, the drying element comprises one or more drying agents, such as silica, activated charcoal, calcium sulfate, calcium chloride, zeolite, alcohol, acetone, and the like. In some embodiments, for example, the drying element comprises one or more silica gel beads.

The pathogen detection devices of the present disclosure also include at least one charging electrode that communicates with the cavity. The charging electrode charges at least some of the pathogenic particles in the concentrated pathogenic particle composition to produce a charged pathogenic particle composition when the concentrated pathogenic particle composition moves at least proximal to the charging electrode. In addition, the pathogen detection devices of the present disclosure also include at least one detecting electrode that communicates with the cavity. The detecting electrode captures at least some of the pathogenic particles in the charged pathogenic particle composition to produce a captured pathogenic particle composition when the charged pathogenic particle composition moves at least proximal to (e.g., through, over, under, around, and/or the like) the detecting electrode.

In certain embodiments, the charging electrode and/or the detecting electrode is porous. In some embodiments, the charging electrode and/or the detecting electrode comprises one or more nanotubes and/or nanowires. In certain embodiments, the charging electrode and/or the detecting electrode comprises at least about 1000 nanotubes and/or at least about 1000 nanowires. In certain embodiments, the nanotubes and/or nanowires occupy a volume of at least about 2.0 mm³. In some embodiments, the nanotubes and/or nanowires comprise cupric oxide nanowires (CuO NWs), carbon nanotubes (CNTs) and/or carbon nanowires (CNWs). In some embodiments, pathogenic particles are detected via charge accumulation at detecting electrodes. Optionally, CuO NWs are used for photoelectrochemical (PEC) sensing at detecting electrodes in which photocurrent is measured upon irradiation with visible wavelength light. More specifically, in some implementations of these detection methods, when visible wavelength range light irradiates CuO nanowires, photoelectric current is generated by virtue of CuO NWs being p-type semiconductors. So, in certain embodiments of the pathogen detection methods and related aspects disclosed herein, the charged pathogenic particles captured at detecting electrodes produce different responses in the photocurrent generated. These changes in response are typically directly proportional to the number of charged pathogenic particles captured at detecting electrodes. Photoelectrochemical sensing is also described in, for example, Zhan et al., "Vertical CuO nanowires array electrodes: Visible light sensitive photoelectrochemical biosensor of ethanol detection," *Mater Sci Semicond Process,* 85:90-97 (2018) and Song et al., "High-performance copper oxide visible-light photodetector via grain-structure model," *Sci Rep,* 9:7334 (2019). In certain embodiments, at least some of the nanotubes and/or nanowires are coated. In certain embodiments, for example, at least some of the nanotubes and/or nanowires are collagen coated. In some embodiments, the charging electrode is structured to generate a negative charge. In certain embodiments, the detecting electrode is structured to generate a positive charge.

In certain embodiments, the detecting electrode include conjugated or otherwise operably connected binding agents that substantially specifically bind the pathogenic particles to thereby capture at least some of the pathogenic particles in the charged pathogenic particle composition as the charged pathogenic particle composition moves at least proximal to the detecting electrode to produce the captured pathogenic particle composition. In certain embodiments, the binding agents comprise at least one cognate receptor (e.g., an antibody or other biomolecule) of the pathogenic particles. In certain embodiments, the detecting electrode nanotubes and/or nanowires and the binding agents or the ACE2 receptors are operably connected to the nanotubes and/or nanowires. In some embodiments, the binding agents or the ACE2 receptors are expressed on the surface of cells that are operably connected to the detecting electrode. In certain embodiments, for example, the detecting electrode includes nanotubes and/or nanowires and the cells that are conjugated with the nanotubes and/or nanowires.

The pathogen detection devices of the present disclosure also include a controller operably connected, or connectable to, at least to the detecting electrode. The controller detects at least some of the pathogenic particles in the captured pathogenic particle composition when the captured pathogenic particle composition is produced. Exemplary controllers are described further herein. In addition, the pathogen detection devices of the present disclosure also include a power source (e.g. an AC or DC power source) operably connected, or connectable to, at least to the charging electrode, the detecting electrode, and/or the controller. In some embodiments, for example, power sources include rechargeable or other batteries. In some embodiments, the controller and/or power source is configured to effect application of a voltage difference between the charging electrode and the detecting electrode in a range of about 0.1 volts (Vs) to about 25 Vs (e.g., a range of about 1 V to about 10 Vs, or the like).

In certain embodiments, the pathogen detection device comprises a tri-layer electro-aerodynamic device. See, e.g., FIGS. 2 and 3. In some of the detection devices or systems disclosed herein, the controller is configured to effect quantifying a number of the pathogenic particles or the SARS-CoV-2 particles in the aerosol sample. In certain embodiments, the controller detects an electrical signal induced by the pathogenic particles (e.g., by binding the pathogenic particles) in the captured pathogenic particle composition or by the SARS-CoV-2 particles (e.g., by binding the SARS-CoV-2 particles) in the captured SARS-CoV-2 particle composition. In certain embodiments, the controller is configured to subtract at least one background signal from the electrical signal that is detected, for example, to improve the signal-to-noise ratio.

In some embodiments, the body structures of pathogen detection devices include a reusable portion and a disposable portion. See, e.g., FIGS. 2 and 3. The disposable portion typically comprises at least portions of the opening, the cavity, the drying element, the charging electrode, and the detecting electrode. In some of the detection devices or systems disclosed herein, the reusable portion comprises at least one result indicator (e.g., an indicator light, a display screen, etc.) operably connected, or connectable, at least to the detecting electrode and/or to the controller, which result indicator indicates when the pathogen or the SARS-CoV-2 is detected. In some of the detection devices or systems disclosed herein, the reusable portion comprises at least one handle. In some embodiments, the systems disclosed herein include multiple pathogen detection devices and/or multiple SARS-CoV-2 detection devices operably connected, or connectable to, the controller (e.g., as part of a pathogen (e.g., SARS-CoV-2) surveillance or monitoring network). Exemplary pathogen surveillance or monitoring networks are described further herein.

Pathogen detection device components (e.g., body structure portions, electrodes, drying elements, etc.) are optionally formed by various fabrication techniques or combinations of such techniques including, e.g., extrusion, injection molding, cast molding, stamping, machining, embossing, engraving, etching (e.g., electrochemical etching, etc.), 3D printing, or other techniques. These and other suitable fabrication techniques are generally known in the art and described in, e.g., Molinari et al. (Eds.), Metal Cutting and High Speed Machining, Kluwer Academic Publishers (2002), Chung, Extrusion of Polymers: Theory and Practice, Hanser-Gardner Publications (2000), Altintas, Manufacturing Automation: Metal Cutting Mechanics, Machine Tool Vibrations, and CNC Design, Cambridge University Press (2000), Stephenson et al., Metal Cutting Theory and Practice, Marcel Dekker (1997), Fundamentals of Injection Molding, W. J. T. Associates (2000), Whelan, Injection Molding of Thermoplastics Materials, Vol. 2, Chapman & Hall (1991), Rosato, Injection Molding Handbook, 3rd Ed., Kluwer Academic Publishers (2000), Fisher, Extrusion of Plastics, Halsted Press (1976), and Redwood et al., The 3D Printing Handbook: Technologies, 1st Ed., Design and Applications, 3D Hubs (2017), which are each incorporated by reference. Exemplary materials optionally used to fabricate device components include, e.g., metal (e.g., magnetic and/or non-magnetic), glass, wood, polymethylmethacrylate, polyethylene, polydimethylsiloxane, polyetheretherketone, polytetrafluoroethylene, polystyrene, polyvinylchloride, polypropylene, polysulfone, polymethylpentene, and polycarbonate, among many others. In some embodiments, following fabrication, device components are optionally further processed, e.g., by painting, coating surfaces with a hydrophilic coating or a hydrophobic coating, or the like.

In some embodiments, the pathogen detection devices described herein are provided as components of kits. In some embodiments, kits also include one or more drying agents, replacement disposable portions of pathogen detection devices, batteries or another power source, operational instructions, and/or suitable packaging.

The present disclosure also provides various methods of detecting pathogens (e.g., virus, bacteria, etc.) in aerosol samples. To illustrate, FIG. 4 is a flow chart that schematically depicts exemplary method steps according to some aspects disclosed herein. As shown, method 400 includes moving an aerosol sample that includes pathogenic particles (e.g., one or more virus (e.g., SARS-CoV-2), one or more bacteria, and/or the like) at least partially through a pathogen detection device (e.g., comprising a tri-layer electro-aerodynamic device or the like as described herein) in step 402. Typically, method 400 includes obtaining the aerosol sample from a subject (e.g., a patient suspected of having SARS-CoV-2 exposing or a related infection), for example, via an opening in a device. In some embodiments, for example, method 400 include moving (e.g., flowing or the like) the aerosol sample at least partially through the detection device by having a subject exhaling, spitting, sneezing, coughing, and/or otherwise introducing the aerosol sample into the detection device via an opening. The aerosol sample generally include liquid droplets that have diameters in a range of about 0.1 μm to about 25 μm (e.g., about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, or about 24 μm in diameter). The liquid droplets comprise the pathogenic particles or the SARS-CoV-2 particles.

Method 400 also includes removing at least a portion of an aqueous phase from the aerosol sample (e.g., substantially dehydrating the aerosol sample) as the aerosol sample moves at least proximal to the drying element of the pathogen detection device to produce a concentrated pathogenic particle composition in step 404. Method 400 also includes charging at least some of the pathogenic particles in the concentrated pathogenic particle composition as the concentrated pathogenic particle composition moves at least proximal to the charging electrode to produce a charged pathogenic particle composition in step 406. In addition, method 400 also includes capturing at least some of the pathogenic particles in the charged pathogenic particle composition as the charged pathogenic particle composition moves at least proximal to the detecting electrode to produce a captured pathogenic particle composition in step 408, and detecting at least some of the pathogenic particles (e.g., SARS-CoV-2 particles) in the captured pathogenic particle composition to thereby detect the pathogen in the aerosol sample.

In certain embodiments, method 400 includes quantifying a number of the pathogenic particles or the SARS-CoV-2 particles in the aerosol sample. In some embodiments, for example, method 400 includes quantifying a number of the pathogenic particles or the SARS-CoV-2 particles in the aerosol sample using the formula:

$$N=kQ/n,$$

where Q is an accumulated charge calculated by integrating a detected current signal over a course of one measurement, n is an average charge number of the pathogenic particles or the SARS-CoV-2 particles, and k is a coefficient determined by charging/detection efficiencies of the charging and detecting electrodes. Typically, the pathogenic particles in the captured pathogenic particle composition or the SARS-CoV-2 particles in the captured SARS-CoV-2 particle composition induce an electrical signal that is detected in step 410. In certain embodiments, method 400 includes subtracting at least one background signal from the electrical signal that is detected in step 410.

In some embodiments, method 400 also includes administering at least one therapy to a subject when the pathogen (e.g., SARS-CoV-2) is detected in the aerosol sample obtained from the subject, for example, to treat the subject for an infection with the pathogen. In certain embodiments, method 400 includes repeating one or more steps for different aerosol samples. In some of these embodiments, the pathogen detection device or the SARS-CoV-2 detection device is sanitized before repeating steps for a given different aerosol sample to at least minimize carryover contamination from a previous aerosol sample. In certain embodiments, method 400 includes completing steps 402-410 in less than about five minutes.

In some embodiments, the pathogen detection device or the SARS-CoV-2 detection device includes a reusable portion and a disposable portion. In these embodiments, the disposable portion typically includes the drying element, the charging electrode, and the detecting electrode, as described herein. In some embodiments, method 400 includes disposing of the disposable portion after performing steps 402-410. In these embodiments, method 400 also generally includes replacing the used disposable portion with a new, unused disposable portion such that the device can be reused with a different aerosol sample. In certain embodiments, the reusable portion comprises a result indicator (e.g., comprising a light, a display screen, and/or the like) operably connected, or connectable, at least to the detecting electrode of a device. In these embodiments, method 400 also typically includes indicating when the pathogen or the SARS-CoV-2 is detected using the result indicator, e.g., to notify a healthcare provider or other user with notice of the detection.

Figure 5:
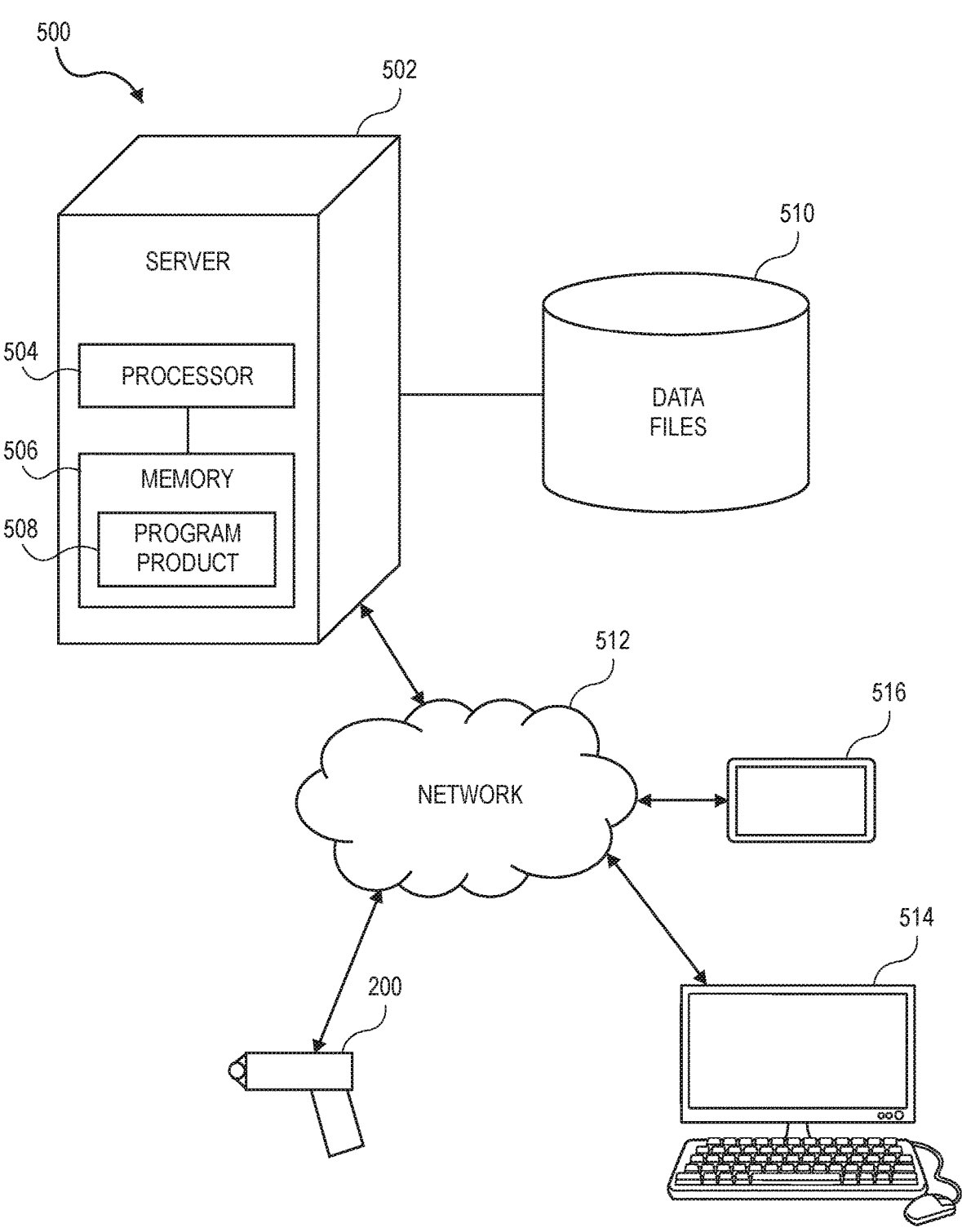
FIG. 5 is a schematic diagram of an exemplary system suitable for use with certain aspects disclosed herein.

The present disclosure also provides various systems and computer program products or machine readable media. In some aspects, for example, the methods described herein are optionally performed or facilitated at least in part using systems, distributed computing hardware and applications (e.g., cloud computing services), electronic communication networks, communication interfaces, computer program products, machine readable media, electronic storage media, software (e.g., machine-executable code or logic instructions) and/or the like. To illustrate, FIG. 5 provides a schematic diagram of an exemplary system suitable for use with implementing at least aspects of the methods disclosed in this application. As shown, system 500 includes at least one controller or computer, e.g., server 502 (e.g., a search engine server), which includes processor 504 and memory, storage device, or memory component 506, and one or more other communication devices 514, 516, (e.g., client-side computer terminals, telephones, tablets, laptops, other mobile devices, etc. (e.g., for receiving data for further analysis, etc.)) positioned remote from pathogen detection device 200, and in communication with the remote server 502, through electronic communication network 512, such as the Internet or other internetwork. Communication devices 514, 516 typically include an electronic display (e.g., an internet enabled computer or the like) in communication with, e.g., server 502 computer over network 512 in which the electronic display comprises a user interface (e.g., a graphical user interface (GUI), a web-based user interface, and/or the like) for displaying results upon implementing the methods described herein. In certain aspects, communication networks also encompass the physical transfer of data from one location to another, for example, using a hard drive, thumb drive, or other data storage mechanism. System 500 also includes program product 508 stored on a computer or machine readable medium, such as, for example, one or more of various types of memory, such as memory 506 of server 502, that is readable by the server 502, to facilitate, for example, a guided search application or other executable by one or more other communication devices, such as 514 (schematically shown as a desktop or personal computer). In some aspects, system 500 optionally also includes at least one database server, such as, for example, server 510 associated with an online website having data stored thereon (e.g., entries corresponding to more reference images, indexed therapies, etc.) searchable either directly or through search engine server 502. System 500 optionally also includes one or more other servers positioned remotely from server 502, each of which are optionally associated with one or more database servers 510 located remotely or located local to each of the other servers. The other servers can beneficially provide service to geographically remote users and enhance geographically distributed operations.

As understood by those of ordinary skill in the art, memory 506 of the server 502 optionally includes volatile and/or nonvolatile memory including, for example, RAM, ROM, and magnetic or optical disks, among others. It is also understood by those of ordinary skill in the art that although illustrated as a single server, the illustrated configuration of server 502 is given only by way of example and that other types of servers or computers configured according to various other methodologies or architectures can also be used. Server 502 shown schematically in FIG. 5, represents a server or server cluster or server farm and is not limited to any individual physical server. The server site may be deployed as a server farm or server cluster managed by a server hosting provider. The number of servers and their architecture and configuration may be increased based on usage, demand and capacity requirements for the system 500. As also understood by those of ordinary skill in the art, other user communication devices 514, 516 in these aspects, for example, can be a laptop, desktop, tablet, personal digital assistant (PDA), cell phone, server, or other types of computers. As known and understood by those of ordinary skill in the art, network 512 can include an internet, intranet, a telecommunication network, an extranet, or world wide web of a plurality of computers/servers in communication with one or more other computers through a communication network, and/or portions of a local or other area network.

As further understood by those of ordinary skill in the art, exemplary program product or machine readable medium 508 is optionally in the form of microcode, programs, cloud computing format, routines, and/or symbolic languages that provide one or more sets of ordered operations that control the functioning of the hardware and direct its operation. Program product 508, according to an exemplary aspect, also need not reside in its entirety in volatile memory, but can be selectively loaded, as necessary, according to various methodologies as known and understood by those of ordinary skill in the art.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 508 implementing the functionality or processes of various aspects of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Program product 508 is optionally copied from the computer-readable medium to a hard disk or a similar intermediate storage medium. When program product 508, or portions thereof, are to be run, it is optionally loaded from their distribution medium, their intermediate storage medium, or the like into the execution memory of one or more computers, configuring the computer(s) to act in accordance with the functionality or method of various aspects. All such operations are well known to those of ordinary skill in the art of, for example, computer systems.

To further illustrate, in certain aspects, this application provides systems that include one or more processors, and one or more memory components in communication with the processor. The memory component typically includes one or more instructions that, when executed, cause the processor to provide information that causes at least one result, data, and/or the like to be displayed or otherwise indicated (e.g., via a result indicator of device 200 and/or via communication devices 514, 516 or the like) and/or receive information from other system components and/or from a system user (e.g., via communication devices 514, 516, or the like).

In some aspects, program product 508 includes non-transitory computer-executable instructions which, when executed by electronic processor 504 perform at least: charging at least some pathogenic particles in a concentrated pathogenic particle composition as the concentrated pathogenic particle composition moves at least proximal to the charging electrode to produce a charged pathogenic particle composition; capturing at least some of the pathogenic particles in the charged pathogenic particle composition as the charged pathogenic particle composition moves at least proximal to the detecting electrode to produce a captured pathogenic particle composition; and/or detecting at least some of the pathogenic particles in the captured pathogenic particle composition.

Figure 6:
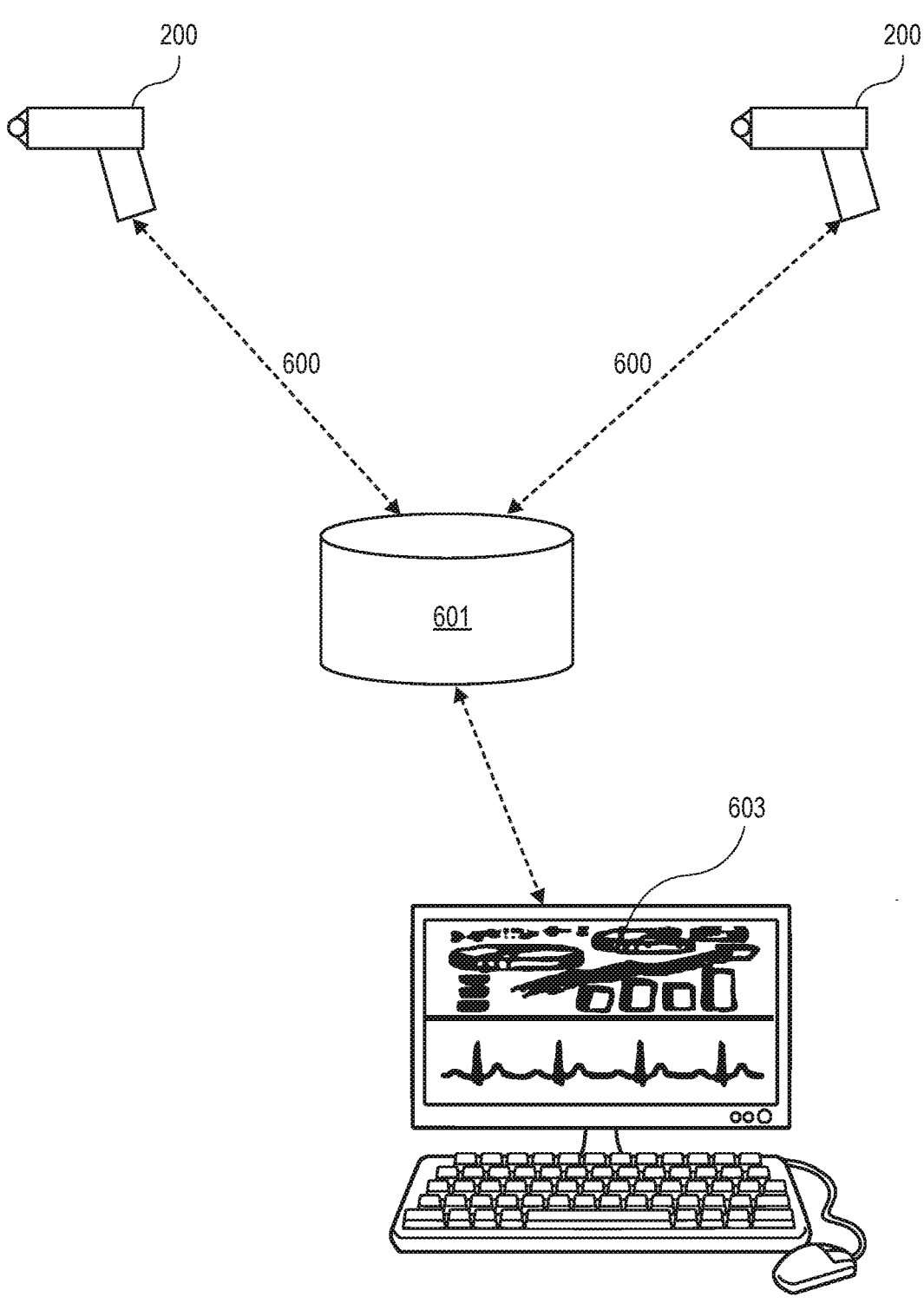
FIG. 6 schematically shows a wireless communication network for gathering pathogen detection data from multiple subjects according to one exemplary embodiment.

To further illustrate, FIG. 6 schematically illustrates that multiple pathogen detection devices 200 are optionally provided to test multiple subjects with wireless communications capability so as to communicate (as indicated by dashed-lines 600) with a computer 603, via for example, a server 601. In some embodiments, this configuration is used to monitor randomized, controlled clinical trials, to provide surveillance or monitoring potential epidemics/pandemics across remotely located populations of subjects. While not limited to any particular embodiment, such communication may be via electrical communication (such as via a USB cable) or via electromagnetic communication via Wi-Fi, Bluetooth, or the like. In one example, computer 603 may include a processor that executes software instructions for communicating with pathogen detection devices 200. As such, remote monitoring of infectious disease detection is also optionally done remotely by via pathogen detection devices 200. While not limited to any particular embodiment, computer 603 may be a desktop computer, notebook computer, smart phone, tablet, a virtual reality device, a mixed reality device and server 601 may be a cloud server or another format. Computer 603 may communicate with pathogen detection devices 200 via the internet.

Additional details relating to computer systems and networks, databases, and computer program products are also provided in, for example, Peterson, *Computer Networks: A Systems Approach*, Morgan Kaufmann, 5th Ed. (2011), Kurose, *Computer Networking: A Top-Down Approach*, Pearson, 7*th* Ed. (2016), Elmasri, *Fundamentals of Database Systems*, Addison Wesley, 6th Ed. (2010), Coronel, *Database Systems: Design, Implementation, & Management*, Cengage Learning, 11*th* Ed. (2014), Tucker, *Programming Languages*, McGraw-Hill Science/Engineering/Math, 2nd Ed. (2006), and Rhoton, *Cloud Computing Architected: Solution Design Handbook*, Recursive Press (2011), which are each incorporated by reference in their entirety.

EXAMPLE 1

Figure 7:
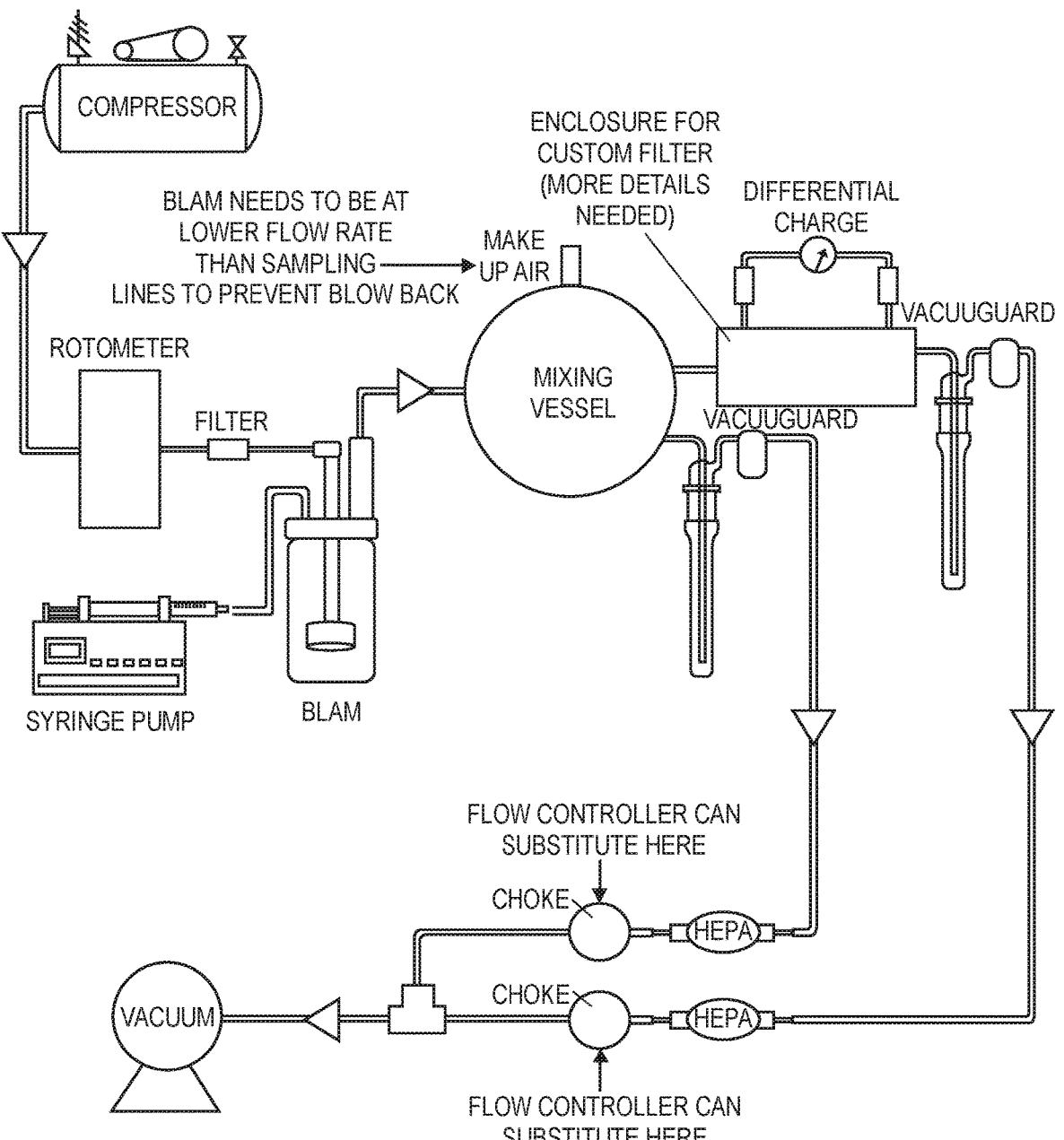
FIG. 7 schematically depicts an aerodynamic measurement apparatus for analyzing SARS-CoV-2 in aerosol samples according to one exemplary embodiment.

To mimic the aerosols generated by coughing, an aerodynamic measurement apparatus was built by using an aerosol generator (Blaustein Atomizing Modules, BLAM) (FIG. 7). This system generated aerosols containing liquid droplets of 0.4 μm-5 μm which is consistent with the aerosols generated from human cough [Zayas et al., "Cough aerosol in healthy participants: fundamental knowledge to optimize droplet-spread infectious respiratory disease management, *BMC Pulmonary Medicine,* 12(1) (2012)]. Virus particles are introduced into the BLAM by using an automized syringe pump with control over the flow rate, allowing for tuning the concentration of virus within the generated aerosol. It has been shown that such a strategy can produce continuous and stable aerosol streams of viable coronavirus for hours [Van Doremalen et al., "Aerosol and Surface Stability of SARS-CoV-2 as Compared with SARS-CoV-1,*" New England Journal of Medicine.* (2020)].

Figure 8A:
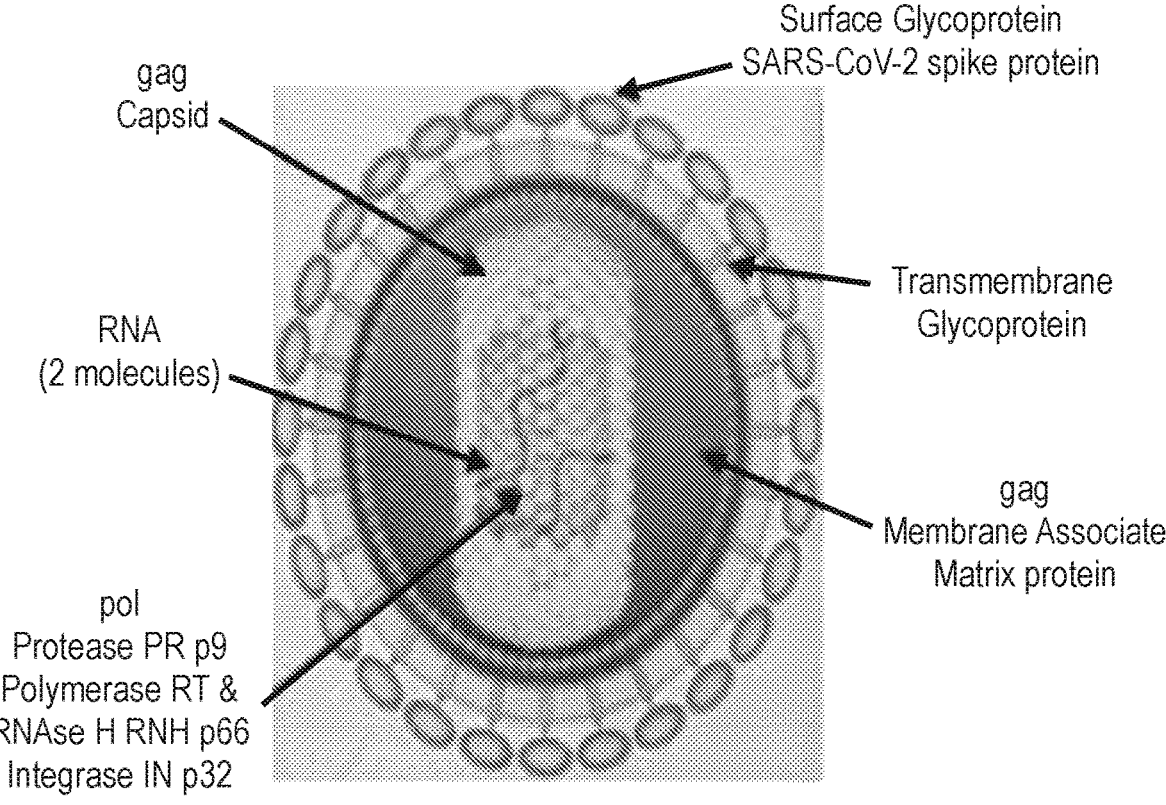
FIG. 8A schematically illustrates a scheme for the fabrication of a SARS-CoV-2 spike protein pseudo typed FIV according to one exemplary embodiment.
Figure 8B:
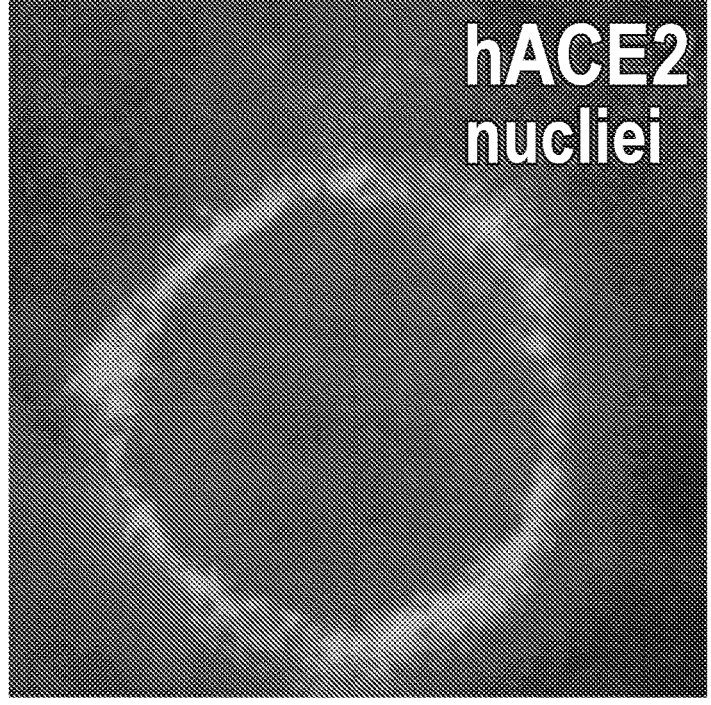
FIG. 8B shows a confocal microscopy image of GFP tagged wild-type ACE2 showing that the protein is localized on the cell surface of an expressing plasmid transfected HEK293 cell.
Figure 8C:
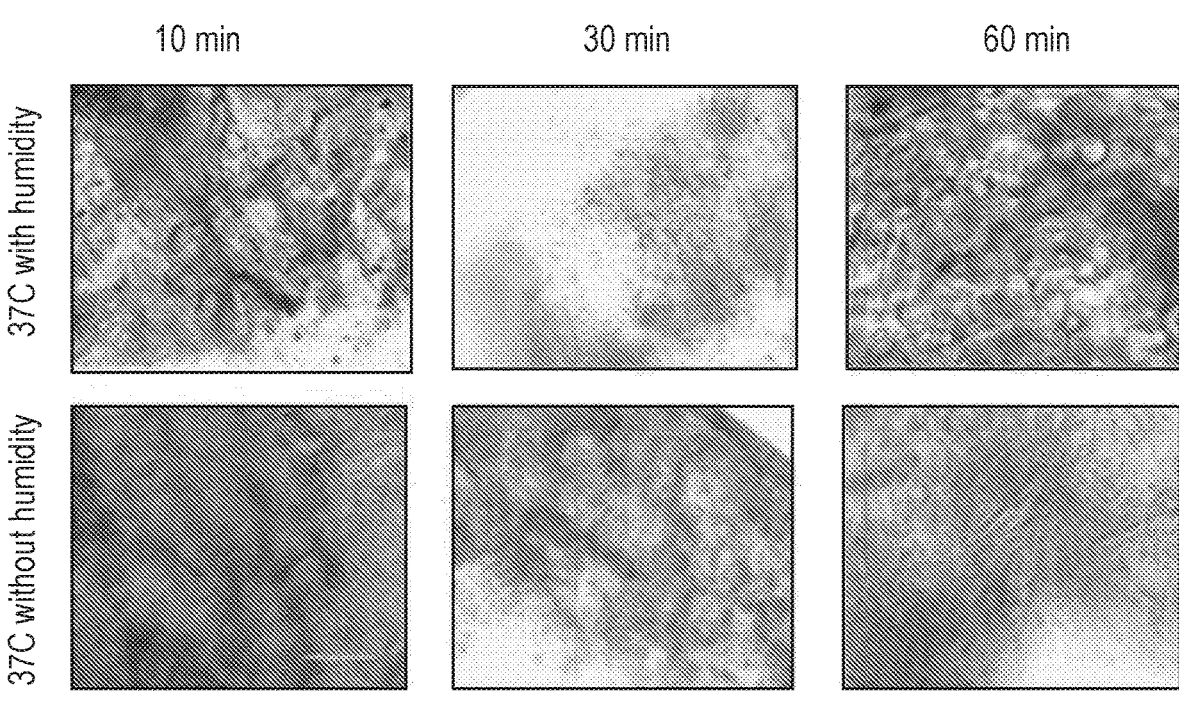
FIG. 8C show images of a Typan blue dye assay for viability test of HEK293 cells cultured on porcine SIS membrane in air at 10 minutes, 30 minutes, and 60 minutes with and without humidity.

Studies to validate the principle of using ACE2 to detect SARS-CoV-2 in biosensors have been performed. A SARS-CoV-2 spike protein (S protein), pseudotyped feline immunodeficient virus (FIV), termed "pseudo-CoV-2," in which the S protein from the corona virus serves as an envelope of the FIV was generated (FIG. 8 (panel a)). In addition, a cell line was successfully generated by transfecting human ACE2 expressing plasmid into HEK293 cells, so that the human ACE2 is expressed and located on the cell surface for the SARS-CoV-2 binding (FIG. 8 (panel b)). In order to use these cells as bait for the coronavirus, their viability was tested in air by loading the ACE2 expressing HEK293 cells on a porous porcine SIS membrane. Trypan blue assay shows that >50% of the cells are viable for up to 1 hour at 37° C., and even more when it was under humidity control (FIG. 8 (panel c)).

In the next step, the ACE2 expressing HEK293 cells grown on the SIS membrane in air are targeted with the pseudo CoV-2 virus. FIV with alternative envelope are used as the negative control. This is performed by spraying the pseudo CoV-2 aerosols onto the SIS membrane. The pseudo CoV-2 virus is labeled with enhanced green fluorescence protein (eGFP) as a reporter and their interaction with the ACE2 receptor expressed on HEK293 and the subsequent endocytosis process are tracked by using confocal microscopy imaging (FIG. 8 (panel b)). Besides using HEK cells for recognition of the coronavirus, other similar studies on the SIS membrane directly modified with ACE2 through bioconjugation are also performed. After validation of the effective binding, similar targeting experiments for both HEK cells and ACE2 supported on the porous electrodes with the surface modified with collagen are also carried out. The effectiveness of targeting is compared by, for example, measuring eGFP intensity in the confocal microscopy images collected after the electrodes are exposed to the aerosol containing the pseudo CoV-2.

EXAMPLE 2

Figure 9:
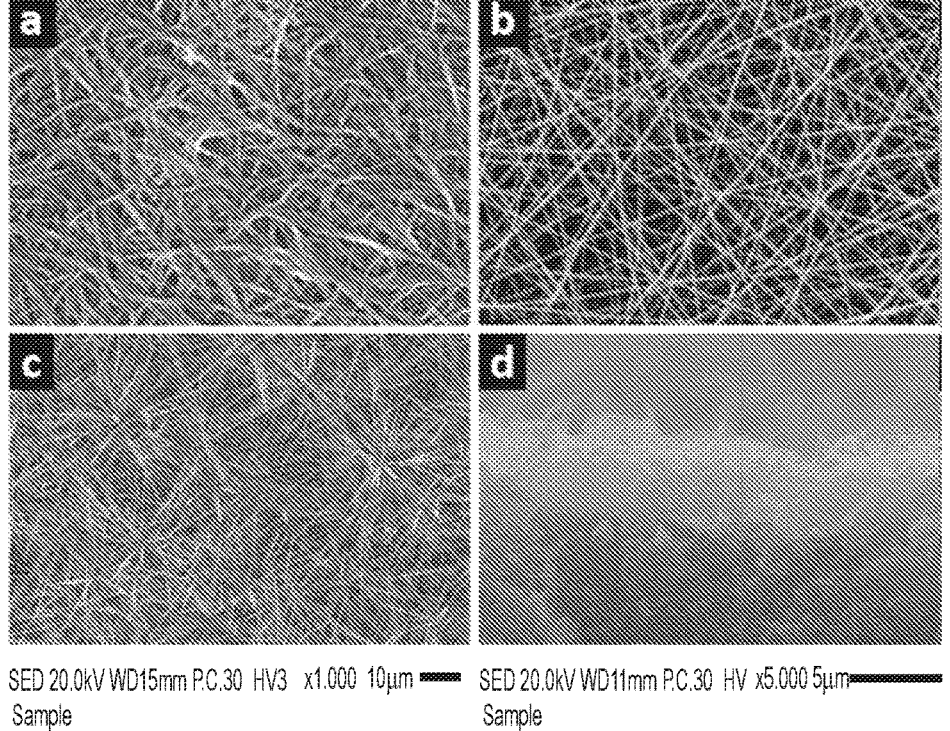
FIG. 9 (panels a-d) show SEM images of CNT aerogels with (panel a) and without (panel b) collagen modification, and CuO nanowires grown on GDEs from a top view (panel c) and from a cross-sectional view (panel d).

In this study, the porous electrodes are fabricated by using low-cost one-dimensional nanomaterials such as CNTs and CuO nanowires (FIG. 9) [Zayas et al., "Cough aerosol in healthy participants: fundamental knowledge to optimize droplet-spread infectious respiratory disease management, *BMC Pulmonary Medicine,* 12(1) (2012)]. CNTs are processed into aerogels to achieve high porosity (e.g., >95%), allowing for efficient interactions with the airborne pathogens for charging and detection. Semiconductor CuO nanowires (p-type with a bandgap of 1.2 eV) are grown on gas diffusion electrodes by using a facile hydrothermal method, which can be readily applied to the proposed biosensors described herein. An advantage of such semiconductor nanowires is utilizing the gating effect of pathogen binding to modulate their conductivity, which can allow for the design of field-effect transistor (FET) type of detectors [Park et al., "Detection of airborne viruses using electro-aerodynamic deposition and a field-effect transistor," *Scientific Reports,* 5(1) (2015)]. CuO nanowires are also compatible with optical transducers (such as optical density and fluorescent spectrometers), which are optionally adapted for use as alternative detectors. The use of highly porous electrodes made of the 1D nanomaterials allows for detection of coronavirus at low concentrations (e.g., <100 $TCID_{50}$ (the tissue culture 50% infectious dose) per $m^3$ air).

The surface of these porous electrodes is modified with collagen by washing coating to reduce undesired interference due to nonspecific bindings. These electrodes are used to fabricate the aerosol biosensors or devices described herein. Various parameters, including the porosities of the two electrodes (charging and detecting), density of HEK cells or ACE2 loading, humidity (controlled by tailoring the diffusion dryer media) and bias voltage are systematically tuned to optimize the aerosol biosensor's sensitivity and specificity. Different aerosol flow conditions are created by tuning the air flow rate, aerosol particle size and density, virus concentrations, and/or the like.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, devices, systems, computer readable media, and/or component parts or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

23

What is claimed is:

1. A method of detecting a severe acute respiratory syndrome coronavirus-2 (SARS-CoV-2) in an aerosol sample, the method comprising:

(a) moving at least one aerosol sample that comprises one or more SARS-CoV-2 particles at least partially through a SARS-CoV-2 detection device that comprises at least one drying element, at least one charging electrode, and at least one detecting electrode, wherein the at least one detecting electrode comprises one or more operably connected angiotensin-converting enzyme 2 (ACE2) receptors and wherein the ACE2 receptors are expressed on the surface of one or more cells that are operably connected to the at least one detecting electrode;

(b) removing at least a portion of an aqueous phase from the aerosol sample as the aerosol sample moves at least proximal to the drying element of the SARS-CoV-2 detection device to produce at least a concentrated SARS-CoV-2 particle composition;

(c) charging at least some of the SARS-CoV-2 particles in the concentrated SARS-CoV-2 particle composition as the concentrated SARS-CoV-2 particle composition moves at least proximal to the at least one charging electrode to produce a charged SARS-CoV-2 particle composition;

(d) capturing at least some of the SARS-CoV-2 particles in the charged SARS-CoV-2 particle composition with the ACE2 receptors as the charged SARS-CoV-2 particle composition moves at least proximal to the at least one detecting electrode to produce a captured SARS-CoV-2 particle composition; and (e) detecting at least some of the SARS-CoV-2 particles in the captured SARS-CoV-2 particle composition, thereby detecting the SARS-CoV-2 in the aerosol sample.

2. The method of claim 1, comprising obtaining the aerosol sample from a subject.

3. The method of claim 1, wherein the at least one drying element comprises at least one diffusion drying element.

4. The method of claim 1, wherein step (b) comprises substantially dehydrating the aerosol sample.

5. The method of claim 1, wherein the at least one detecting electrode comprises one or more nanotubes and/or nanowires and wherein the one or more cells are operably connected to the nanotubes and/or nanowires.

6. The method of claim 1, comprising quantifying a number of the SARS-CoV-2 particles in the aerosol sample using the formula:

$$N=kQ/n,$$

where Q is an accumulated charge calculated by integrating a detected current signal over a course of one measurement, n is an average charge number of the SARS-CoV-2 particles, and k is a coefficient determined by charging/detection efficiencies of the charging and detecting electrodes.

7. The method of claim 1, wherein the SARS-CoV-2 particles in the captured SARS-CoV-2 particle composition induce an electrical signal that is detected in step (e).

8. The method of claim 1, comprising administering at least one therapy to a subject when the SARS-CoV-2 is detected in the aerosol sample obtained from the subject.

9. The method of claim 1, comprising completing steps (a)-(e) in less than about five minutes.

10. The method of claim 1, wherein step (e) comprises detecting the SARS-CoV-2 particles via charge accumulation and/or via photoelectrochemical (PEC) sensing.

11. A severe acute respiratory syndrome coronavirus-2 (SARS-CoV-2) detection device, comprising:

a body structure that comprises at least one cavity and at least one opening that communicates with the cavity, wherein the at least one cavity receives at least one aerosol sample that comprises one or more SARS-CoV-2 particles when the aerosol sample moves through the opening;

at least one drying element that communicates with the cavity, wherein the at least one drying element removes at least a portion of an aqueous phase from the aerosol sample to produce at least a concentrated SARS-CoV-2 particle composition when the aerosol sample moves at least proximal to the drying element;

at least one charging electrode that communicates with the cavity, wherein the at least one charging electrode charges at least some of the SARS-CoV-2 particles in the concentrated SARS-CoV-2 particle composition to produce a charged SARS-CoV-2 particle composition when the concentrated SARS-CoV-2 particle composition moves at least proximal to the charging electrode;

at least one detecting electrode that communicates with the cavity, wherein the at least one detecting electrode comprises one or more operably connected angiotensin-converting enzyme 2 (ACE2) receptors that capture at least some of the SARS-CoV-2 particles in the charged SARS-CoV-2 particle composition to produce a captured SARS-CoV-2 particle composition when the charged SARS-CoV-2 particle composition moves at least proximal to the at least one detecting electrode, wherein the ACE2 receptors are expressed on the surface of one or more cells that are operably connected to the at least one detecting electrode;

at least one controller operably connected, or connectable to, at least to the at least one detecting electrode, wherein the at least one controller detects at least some of the SARS-CoV-2 particles in the captured SARS-CoV-2 particle composition when the captured SARS-CoV-2 particle composition is produced; and, at least one power source operably connected, or connectable to, at least to the at least one charging electrode, the at least one detecting electrode, and/or the at least one controller.

12. The detection device of claim 11, wherein the at least one detecting electrode comprises one or more nanotubes and/or nanowires and wherein the one or more cells are operably connected to the nanotubes and/or nanowires.

13. The detection device of claim 11, wherein the at least one controller is configured to effect quantifying a number of the SARS-CoV-2 particles in the aerosol sample.

14. The detection device of claim 11, wherein the at least one controller detects an electrical signal induced by the SARS-CoV-2 particles in the captured SARS-CoV-2 particle composition.

15. The detection device of claim 11, wherein the body structure comprises a reusable portion and a disposable portion, wherein the disposable portion comprises at least portions of the at least one opening, the at least one cavity, the at least one drying element, the at least one charging electrode, and the at least one detecting electrode.

16. The detection device of claim 11, wherein the detection device is configured to detect the SARS-CoV-2 particles via charge accumulation and/or via photoelectrochemical (PEC) sensing.

17. A kit comprising the detection device of claim 11.

18. A system, comprising:

at least one severe acute respiratory syndrome coronavirus-2 (SARS-CoV-2) detection device that comprises at least one drying element, at least one charging electrode, and at least one detecting electrode, wherein the at least one detecting electrode comprises one or more operably connected angiotensin-converting enzyme 2 (ACE2) receptors, wherein the ACE2 receptors are expressed on the surface of one or more cells that are operably connected to the at least one detecting electrode; and, at least one controller operably connected, or connectable to, at least to the SARS-CoV-2 detection device, wherein the at least one controller comprises, or is capable of accessing, computer readable media comprising non-transitory computer-executable instructions which, when executed by at least one electronic processor perform at least:

26 charging at least some SARS-CoV-2 particles in a concentrated SARS-CoV-2 particle composition as the concentrated SARS-CoV-2 particle composition moves at least proximal to the charging electrode to produce a charged SARS-CoV-2 particle composition, wherein the concentrated SARS-CoV-2 particle composition is produced by removing at least a portion of an aqueous phase from an aerosol sample that comprises the SARS-CoV-2 particles as the aerosol sample moves at least proximal to the at least one drying element of the SARS-CoV-2 detection device;

capturing at least some of the SARS-CoV-2 particles in the charged SARS-CoV-2 particle composition with the ACE2 receptors as the charged SARS-CoV-2 particle composition moves at least proximal to the at least one detecting electrode to produce a captured SARS-CoV-2 particle composition; and detecting at least some of the SARS-CoV-2 particles in the captured SARS-CoV-2 particle composition.

\* \* \* \* \*